United States Patent [19]

Xu

[11] Patent Number: 5,405,608
[45] Date of Patent: Apr. 11, 1995

[54] PHARMACEUTICAL COMPOSITION FOR TREATING THERMAL INJURIES OF WARM BLOODED MAMMALS INCLUDING HUMANS

[76] Inventor: Rongxiang Xu, Rm. 401, 21 Bldg., First District, Fang Gu Yuan, Fangzhuang Xiaoqu, Beijing, China

[21] Appl. No.: 81,399

[22] Filed: Jun. 22, 1993

[30] Foreign Application Priority Data

Jan. 15, 1993 [CN] China .................. 93 1 00276.1

[51] Int. Cl.⁶ ............................................. A61K 35/78
[52] U.S. Cl. .................. 424/195.1; 514/783; 514/787
[58] Field of Search ............. 424/195.1, DIG. 13; 514/783, 787

[56] References Cited

U.S. PATENT DOCUMENTS

| | | | |
|---|---|---|---|
| 4,205,685 | 6/1980 | Yoshida et al. | 128/399 |
| 4,282,250 | 8/1981 | Papageorgiou | 424/311 |
| 4,670,185 | 6/1987 | Fujiwara et al. | 252/311 |
| 4,717,664 | 1/1988 | Yitara et al. | 435/133 |
| 4,917,889 | 4/1990 | Carfy et al. | 424/693.1 |
| 5,162,113 | 11/1992 | Oh et al. | 424/195.1 |
| 5,350,774 | 9/1994 | Palou | 514/783 |

Primary Examiner—Douglas W. Robinson
Assistant Examiner—Howard C. Lee
Attorney, Agent, or Firm—Silverman, Cass & Singer, Ltd.

[57] ABSTRACT

This invention relates to a pharmaceutical composition mainly used for treating thermal injuries of warm blooded mammals and human. It is composed of 3 to 15% by weight of beeswax and 85 to 97% by weight of sesame oil extract of Huangqin, Huanglian, Huangbai, earthworm and poppy capsule. In the sesame oil extract, each of Huangqin, Huanglian, Huangbai, earthworm and poppy capsule is in an amount of 2 to 10 weight percent based upon the total weight of sesame oil. This invention also relates to a process for preparing the pharmaceutical composition.

12 Claims, 9 Drawing Sheets

PHARMACEUTICAL COMPOSITION FOR TREATING THERMAL INJURIES OF WARM BLOODED MAMMALS INCLUDING HUMANS

FIELD OF THE INVENTION

This invention relates to a pharmaceutical composition for treating thermal injuries of warm blooded mammals and human, in particular a pharmaceutical composition containing active constituents extracted from plants and animals and the process for preparing the composition.

BACKGROUND OF THE INVENTION

In 1930s, in the field of trauma surgery, dry and antiinfective therapy was mostly used for treating thermal injuries, especially burn wounds and then followed by surgical skin grafting. With such treating method, doctors succeeded in breaking down the barrier existed for thousands of years, that burn wounds exceeding an area of 30% BSA were very difficult to heal. Later on, thorough investigation on the morbidity of burn shock achieved a successful guidance to the treatment of large area burns and clinically, a therapeutic system of burn surgery had been formed and popularized all over the world and become a routine burn treatment. This treatment described above is hereinafter referred to as "dry therapy" in this paper.

By 1970s, burn surgeons, through experimental researches, began to shake their confidence in the method of dry therapy both theoretically and practically. The main reasons were that dry therapy did not give satisfactory therapeutic results. Patients receiving dry therapy had to suffer great pains and many survivors had deep mental and physical distress.

The inventor points out that dry therapy is wrong both in its theoretical basis and its treating method. Dry therapy considers the thermally injured skin and the stasis zone tissue to be destined to necrose and therefore hastens them to necrose by drying, for the purpose of preventing infections and creating a condition for skin grafting.

Persons having ordinary skill in the art all recognize that dry therapy has many drawbacks. For instance, the wounds without dermis when exposed to air, are directly injured by the air; patients lose a large amount of body fluid; tissue regeneration is inhibited by antibiotics which are used in large doses in dry therapy and removal of eschar and skin grafting often cause iatrogenic injuries, etc.

SUMMARY OF THE INVENTION

The object of this invention is to overcome the draw backs of the existing treating methods and to provide a pharmaceutical composition effective for the repair and the regeneration of the stasis zone tissue after thermal injuries of the skin.

Another object of this invention is to provide a process for preparing the pharmaceutical composition.

The further object of this invention is to provide an application of the pharmaceutical composition for repairing wounds.

The inventor designs a new method for treating thermal injuries, on the basis of the theory of traditional Chinese medicine and modern medicine and calls the new method "moist therapy". Moist therapy considers the stasis zone tissue after thermal injuries to be recoverable. The doctors should make effort to save the tissue and to lessen the injury. Let the thermally injured tissue expose three-dimensionally to a moist environment, which complies with the physiological requirement, is favorable to the removal of necrotic tissue and to the repair and regeneration of the tissues.

In moist therapy, a new novel drug is used. Therefore, this invention relates to a pharmaceutical composition mainly for treating thermal injuries of warm blooded mammals and human which consists of beeswax in an amount of 3 to 15 weight percent and sesame oil extract of ingredients in dry state consisting of Huangqin (baikal skullcap), Huanglian (rhizome of Chinese goldthread or rhizoma Coptidis), Huangbai (cortex phellodendri), earthworm (Dilong) and poppy capsule (Ying su ke) in which each of the ingredients is in an amount of 2 to 10 weight percent based upon the total weight of sesame oil, in an amount of 85 to 97 weight percent based upon the total weight of the composition. In other words, in the oil extract, each of the ingredients in dry state accounts for 2 to 10% by weight.

The above mentioned pharmaceutical composition contains $\beta$-sitosterol accounting for 0.20% to about 1% by weight.

Huangqin (*Scutellaria baicalensis* Georgi) used in the invention is selected one or more from the group of *Scutellaria viscidula* Bge, *Scutellaria amoena* C. H. Wright, *Scutellaria rehderiana* Diels, *Scutellaria ikonnikovii* Juz, *Scutellaria likiangensis* Diels and *Scutellaria hypericifolia* Levl of Labiatae Family. The root is used. (A Dictionary of Chinese Materia Medica, Shanghai Science and Technology Press, 1988, pages 2017 to 2021).

Huanglian (coptis chinensis Franch) used in the invention is selected one or more from the group of *Coptis deltoidea* C. Y. Cheng et Hsiao, *Coptis omeiensis* (Chen) C. Y. Cheng, and *Coptis teetoides* C. Y. Cheng of Ranunculaceae Family. The root is used. (A Dictionary of Chinese Materia Medica, Shanghai Science and Technology Press, 1988, pages 2022 to 2030).

Huangbai (*Phellodendron amurense* Rupr) used in the invention is selected one or more from the group of *Phellodendron chinense* Schneid, *Plellodendron chinense* Scheid var. *glabriusculum* Schneid, *Phellodendron chinense* Schneid var. *omeiense* Huang, *Phellodendron* Schneid var. *yunnanense* Huang and *Phellodendron chinense* Schneid var. *falcutum* Huang. The bark is used. (A Dictionary of Chinese Materia Medica, Shanghai Science and Technology Press, 1988, pages 2031 to 2035).

Earthworm also called Dilong (earth dragon) is selected one or more from the group of *Pheretima aspergillum* (E. Perrier) and *Allolobophora caliginosa* trapezoides (Ant. Duges). The whole worm dried or fresh is used. (A Dictionary of Chinese Materia Medica, Shanghai Science and Technology Press, 1988, pages 2111 to 2114).

Poppy capsule used in the present invention is the dry capsule of *Papaver somniferam* L. The dry capsule is prepared according to the method well-known in the art.

The process for the manufacture of the pharmaceutical composition comprises the following steps: First, Huangqin, Huanglian and Huangbai are cut to pieces, then mixed with earthworm and poppy capsule. Heat sesame oil to boil (120° C. to 180° C.). Add the above mentioned dry raw drugs including Huangqin, Huanglian, Huangbai, earthworm and poppy capsule. Keep the mixture boiling for 30 to 45 minutes. The proportion of the raw drugs to sesame oil is 2-10 to 100. After cooled to ambient temperature, separate the oil extract and discard the residue. A sesame oil extract of the drugs is obtained. Then add beeswax to the oil extract and blend thoroughly. The proportion of beeswax to the sesame oil extract is 3-15% to 85-97%.

The finished product is a light yellow ointment containing no more than 0.01% of water and volatile substances. In liquid state, it is transparent. No particle can be seen under optical microscope.

Its acid value is 3.58±0.20% (determined according to the method described in Pharmacopoeia of PRC, 1985, Appendix page 51,) Saponification value is 178±0.7% (determined according to the method described in Pharmacopoeia of PRC, 1985, Appendix page 51). Softening point: initial softening point is 21° C. to 23° C. (thermistor method) and final softening point is 45° C. to 49° C. (using circulating ball type softening point determination apparatus).

Water content in sesame oil should be within the range of 1:1,000 to 1:10,000. Paraffin content in beeswax should be no more than 20%.

Beeswax is preheated to 100° C. to 180° C. and the mixed with Sesame oil extract.

The pharmaceutical composition manufactured as described above is used primarily for treating thermal injuries of warm blooded mammals and human beings, large area burn wounds in particular, and scalds and chemical burns, etc. In addition, it is also used for healing wounds and ulcers including surface ulcer, infected wound, vaginitis, cervical erosion, hemorrhoid, decubital ulcer, trauma, cold injury, chilblain, etc.

The pharmaceutical composition of the invention can be smeared onto the surface of the lesion area directly to a thickness of about 1 mm. Wound debridement is usually unnecessary. After 4 to 5 hours or longer, the pharmaceutical composition smeared onto the wound becomes liquefied and turns white in color. This implies that the drug has come to work on the wound. The smearing of the drug can be done again. If there is an excessive amount of liquefied substance, wipe it away gently and apply the drug again, until the wound heals completely.

This invention has the following beneficial effects:

The application of the pharmaceutical composition of the invention made from purely natural ingredients has created a new therapy, a new burn therapy in particular, and a new drug for treating thermal injuries. After applying this pharmaceutical composition, the wound is kept moist but not macerated. The necrotic skin layer is liquefied and removed spontaneously. An adequate drainage in the tissue and the wound surface is achieved. The unique dosage form and the action of the drug ensure a constant supply with appropriate concentration of the active constituents to the wound and continuous removal of the excreta from the wound. The wound surface is isolated from the air and is protected from further irritation and injury. The metabolite and the excreta are timely removed.

Furthermore, the pharmaceutical composition of the invention has the effect of relieving pains through a non-narcotic mechanism. 5 to 10 minutes after application of the drug, pains in the wounds can be stopped completely. Thus, the number one difficult problem in the treatment of thermal injuries is resolved.

The pharmaceutical composition of the invention controls bacterial infection through a mechanism other than killing or inhibiting the bacteria. The number two difficult problem in the treatment of thermal injuries is also resolved. Application of large doses of antibiotics is no longer necessary. It is therefore beneficial to the repair and the regeneration of the wound tissue.

The pharmaceutical composition of the invention lessens the progressive necrosis of the wound. A moist environment created by the drug is favorable to the regeneration of the skin and the action of the drug promotes healing, so that deep second degree wounds can be healed without scar formation and large area burn wounds can be healed satisfactorily.

The above mentioned beneficial effects are to be described in detail for better understanding in the following statement.

DETAIL DESCRIPTION OF THE INVENTION

Detailed descriptions of the invention with examples and figures are as follows:

This invention relates to a pharmaceutical composition for treating thermal injuries of warm blooded mammals and human and traumas, hemorrhoids and in particular burn wounds. It is consists of 3 to 15% by weight of beeswax and 85 to 97% by weight of sesame oil extract of Chinese drugs. The percentage is expressed in terms of the total weight of the pharmaceutical composition. The sesame oil extract of Chinese drugs refers to the extract of Huangqin, Huanglian, Huangbai, earthworm and poppy capsule. Each of Huangqin, Huanglian, Huangbai, earthworm and poppy capsule is in an amount of 2 to 10 weight percent based upon the total weight of sesame oil.

Since many constituents in the pharmaceutical composition are not yet very clear. One of the active constituents is confirmed to be β-sitosterol. As well known, β-sitosterol is widely distributed in plants and animals. Its chemical name is stigmast-5-en-3-01(3) with the structure:

Chemical formula: $C_{29}H_{50}O$; Molecular weight: 414.69; Melting point: 140° C. It has the effect of lowering down the blood lipid level in chimpanzee fed with cholesterol. β-sitosterol dioxide is more effective than β-sitosterol (CA 88: 21071f 1978, 86: 418h 1978). It can be used in combination with escin as a local antiinflammatory agent. An injection of 0.2 mg of escin Na salt β-sitosterol complex produced no irritation and decreased carrageenin-induced edema by 13.5% in rats, while escin (0.1 mg) alone produced irritation and increased the edema by 18.6%. The toxicity of escin is reduced by β-sitosterol (CA 86:161298u 1977). β-sitosterol used for treating thermal injuries is thus far not known in literature.

The content of β-sitosterol in the pharmaceutical composition of the invention is 0.20% by weight or more.

The raw materials of the pharmaceutical composition are plants and animals. These raw materials are added to preheated sesame oil. In this process β-sitosterol is probably condensed with the long chain fatty acids in sesame oil to form esters. These esters react with the exudate from the wound and are gradually saponified to give free β-sitosterol. This process facilitates the action of β-sitosterol on the wound tissue.

Beeswax is used because on the one hand, it makes the shape of the ointment and on the other hand, it serves as a preservative owing to its antioxidant and antiacidification effects. Beeswax essence has skin care effect.

It is obvious that all the constituents in the pharmaceutical composition of the invention have therapeutic effects and act synergically in treating thermal injuries.

EXAMPLE 1

Figure 1:
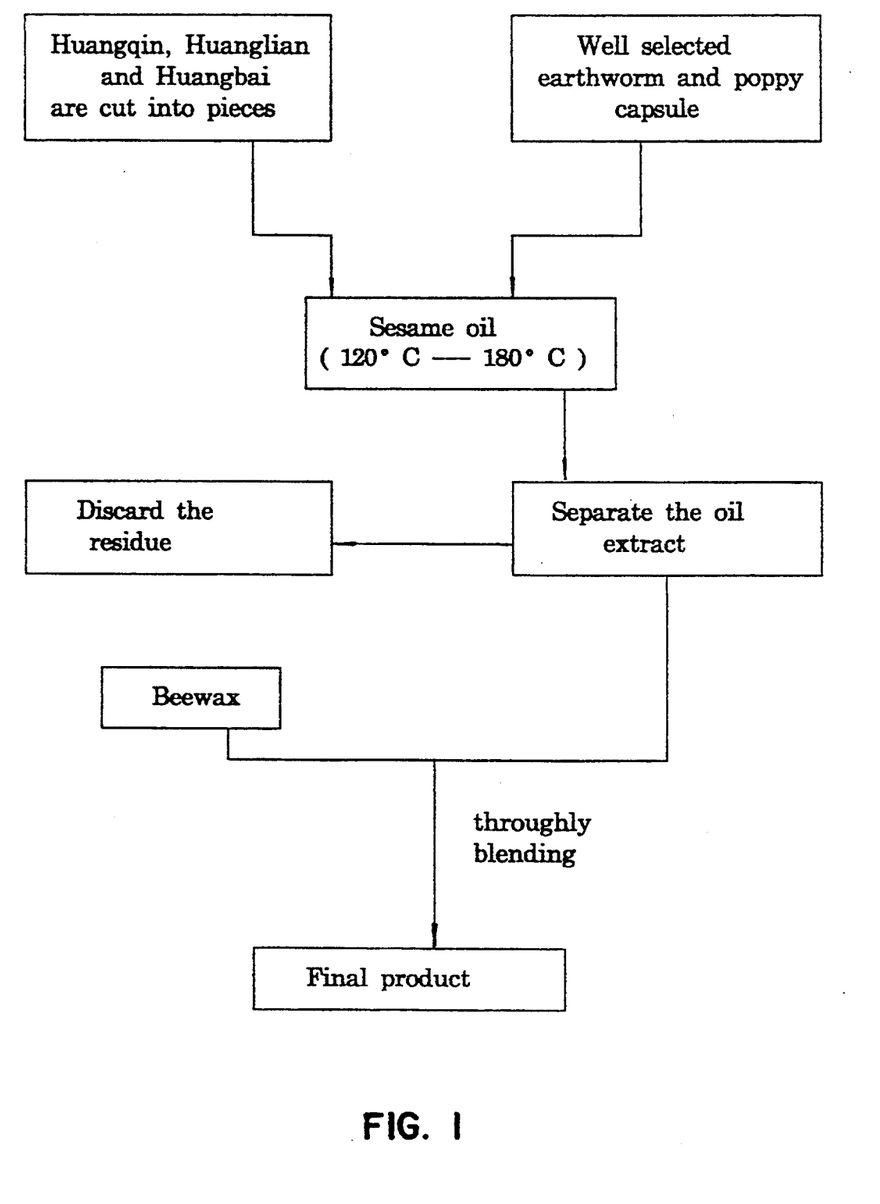
FIG. 1: Flow sheet of the process for preparing the pharmaceutical composition of the invention.

Referred to FIG. 1, 2 kg of Huangqin, 2 kg of Huanglian and 2 kg of Huangbai were selected according to the quality standard described in Pharmacopoeia of PRC and were cut into pieces. Mixed with 2 kg of earthworm and 2 kg of poppy capsule.

100 kg of commercial sesame oil were placed into an extraction pot; heated to 120° C. The mixture of Huangqin, Huanglian, Huangbai, earthworm and poppy capsule was added into the pot. Kept the temperature at 120° C. Stirred for 45 minutes. Cooled to ambient temperature, filtered, discarded the residue. Let to settle. Poured out the transparent oil extract. 1,000 kg of sesame oil extract of the above mentioned drugs was obtained.

Took 85 kg of the above prepared sesame oil extract. Mixed thoroughly with 15 kg of commercial beeswax to obtain 100 kg of the pharmaceutical composition of the invention.

EXAMPLE 2

1 kg of Huangqin, 1 kg of Huanglian and 1 kg of Huangbai were cut into pieces. Added 1 kg of earthworm and 1 kg of poppy capsule and mixed thoroughly. Heated 10 kg of commercial sesame oil to 180° C. Added the mixture of the raw drugs to the oil. Maintained at a temperature of 180° C. for 30 minutes.

Took 9.7 kg of the above prepared sesame oil extract and add 0.3 kg of beeswax preheated to 180° C. Mixed thoroughly to obtain 10 kg of the pharmaceutical composition of the invention.

EXAMPLE 3

Used the method described in example 1. But beeswax was preheated to 100° C. and then mixed with sesame oil extract.

EXPERIMENT 1

Histological Experiment

Classification of burn injury:
First degree—epidermal injury
Second degree—dermal injury
Third degree—full thickness injury A. 7 male and 7 female rabbits, weighing 2 to 2.5 kg were depilated on the dorsolumbar region and were scalded to produce deep second degree wounds with an area of 1 cm$^2$. The animals were divided into 2 groups randomly. Animals in the control group were treated with dry therapy and animals in the experiment group were treated with the pharmaceutical composition of the invention prepared as described in example 1. After 18 days, tissue sections were examined under optical microscope.

Figure 2:
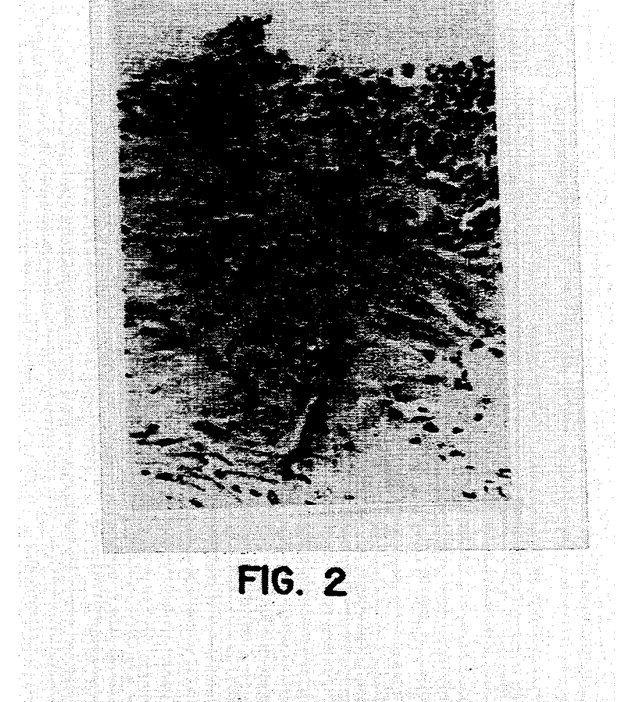
FIG. 2: Rabbits in experiment 1, with deep second degree scalds treated with dry therapy for 18 days. The scalded skin tissue seen under optical microscope (HE×400).
Figure 3:
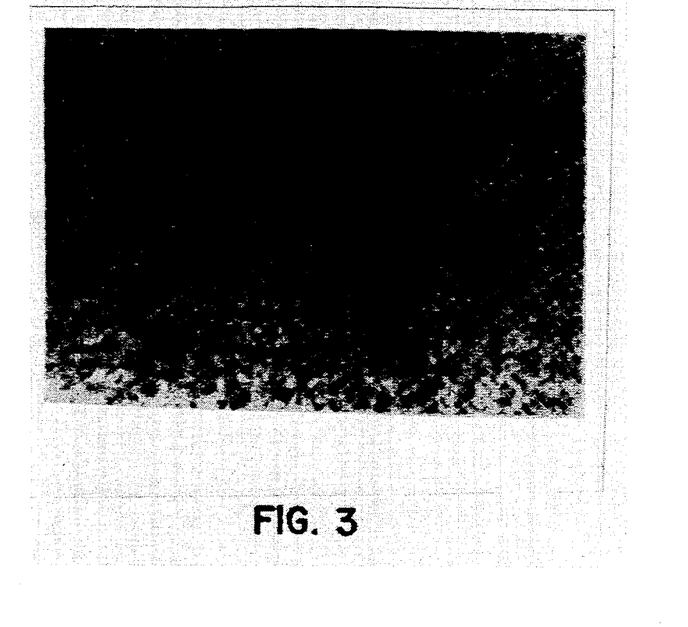
FIG. 3: Rabbits in experiment 1, with deep second degree scalds treated locally with the pharmaceutical composition. The scalded skin tissue on the 18th day, seen under optical microscope (HE×400).

Results: Tissue sections from animals in the control group appeared to have atrophy of granulation tissue, exudation of lobocyte, eosinophilic collagenous fiber and granulation tissue without vitality (see FIG. 2). Tissue sections from animals in experiment group appeared under optical microscope to have active fibroblast proliferation, rich blood vessels and granulation tissue full of vitality (see FIG. 3).

B. 120 healthy pure bred Wistar white rats, weighing 100 to 120 g were depilated on the back and were scalded to produce third degree burn wound in about 20% of the depilated area. 1 ml of a $4 \times 10^8$ suspension of P. aeruginosa was spread on the whole wound surface. The animals were divided into 4 groups and treated with different methods as shown in Table I.

TABLE I

| Group | Number of Animals |
|---|---|
| Control | 30 |
| Treated externally with SD—Ag | 30 |
| Treated externally with the pharmaceutical composition | 30 |
| Treated with heat dry exposed therapy | 30 |

Animals in each group were killed on the 1st, 3rd, 5th, 7th and 9th days. Tissues underneath the wounds were cut with aseptic manipulation for bacteria counting. The average logarithm values of the bacteria counts of the 4 groups were compared. The results revealed that bacteria counts in the tissues of animals treated with the pharmaceutical composition of the invention and animals treated with SD-Ag were significantly less than that of the animals treated with heat dry exposed therapy and the control animals. The difference was statistically significant (P<0.01). But the difference between the control group and the heat dry exposed therapy group was of no significance (P>0.05). The difference between the animals treated with the pharmaceutical composition of the invention and the animals treated with SD-Ag was of no significance (P>0.05).

TABLE II

| Group | Subcrustal bacteria counts<br>Average Logarithm of Bacteria Counts |
|---|---|
| Control | 5.8 ± 2.6 |
| Treated with the pharmaceutical composition of the invention | 3.1 ± 2.8 |
| Treated with SD-Ag | 3.1 ± 3.1 |
| Treated with heat dry exposed therapy | 5.4 ± 2.0 |

Figure 4:
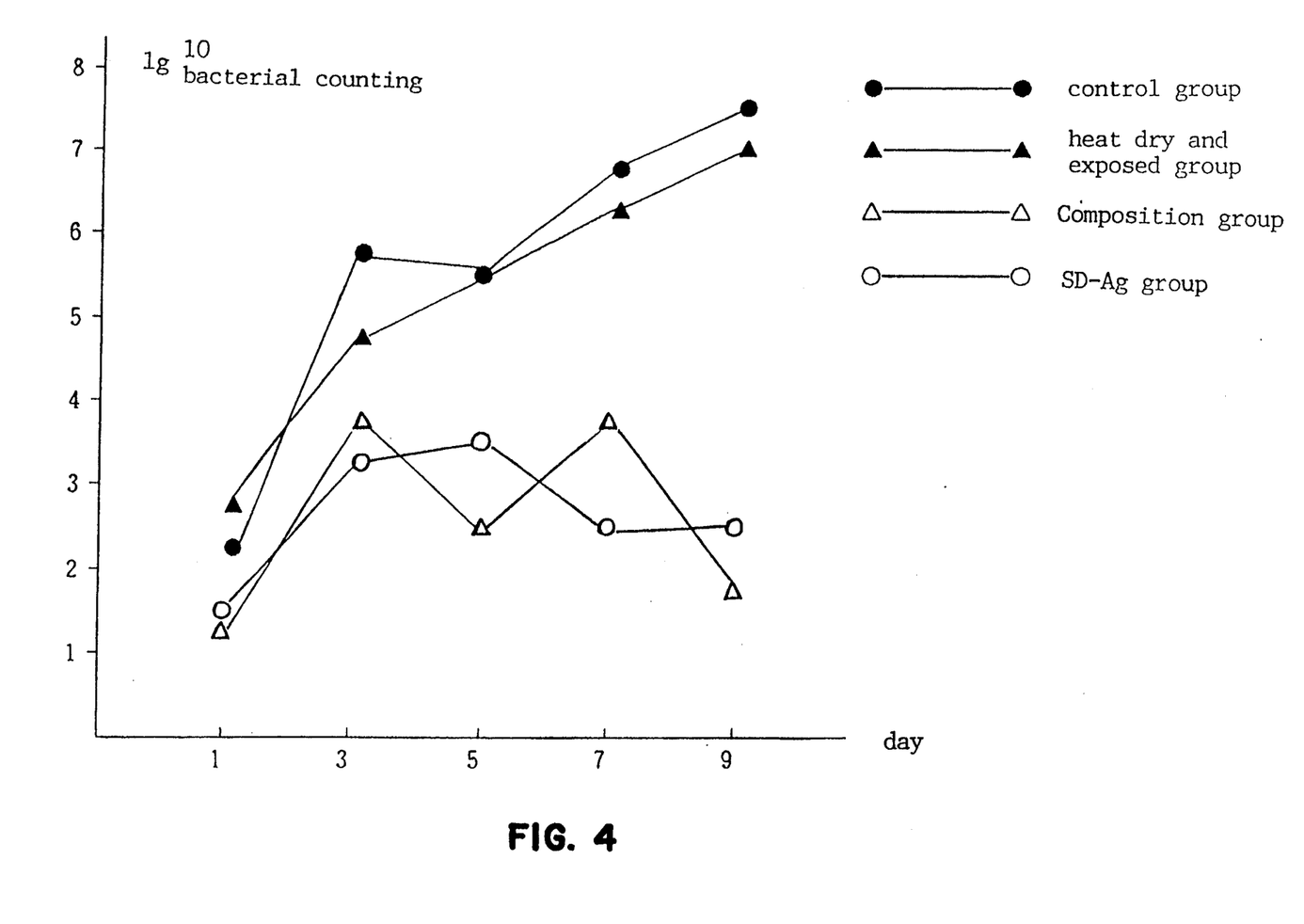
FIG. 4: The relationship between bacteria count in different tissues and the course of the disease.

The relationship between bacteria counts in different tissues and the course of the disease were shown in FIG. 4.

EXPERIMENT 2

Pathological Experiment

Patients with third degree burns long unhealed after skin grafting were treated with the pharmaceutical composition of the invention prepared as described in example 2. Optical micrographs and electron micrographs were taken before and after treatment.
Optical Micrographs (HE×200).

Figure 5:
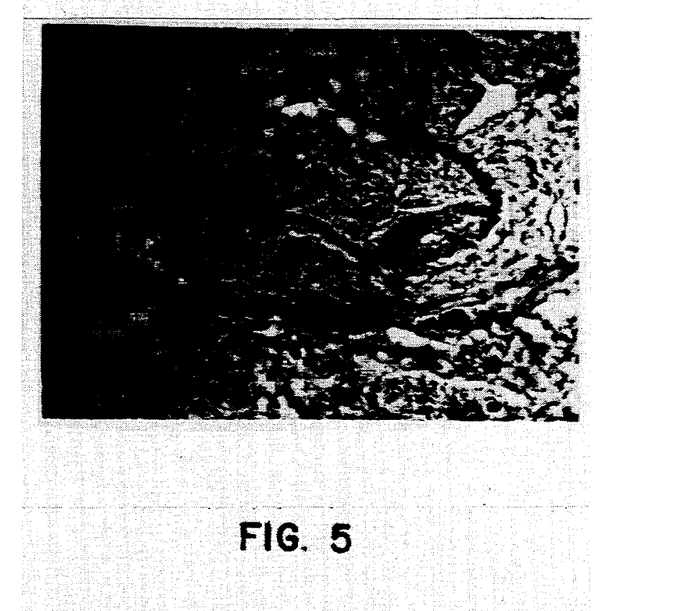
FIG. 5 and 6: Human skin with third degree burn, before treatment, seen under optical microscope (HE×200).
Figure 6:
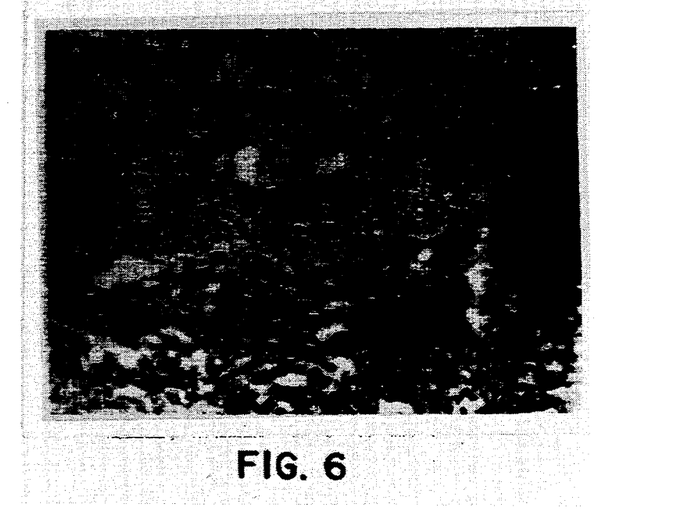

Before treatment: (FIGS. 5 and 6). Around the sweat glands and hair follicles, there were infiltration of inflammatory cells and some focal lesions.

Figures 7, 8:
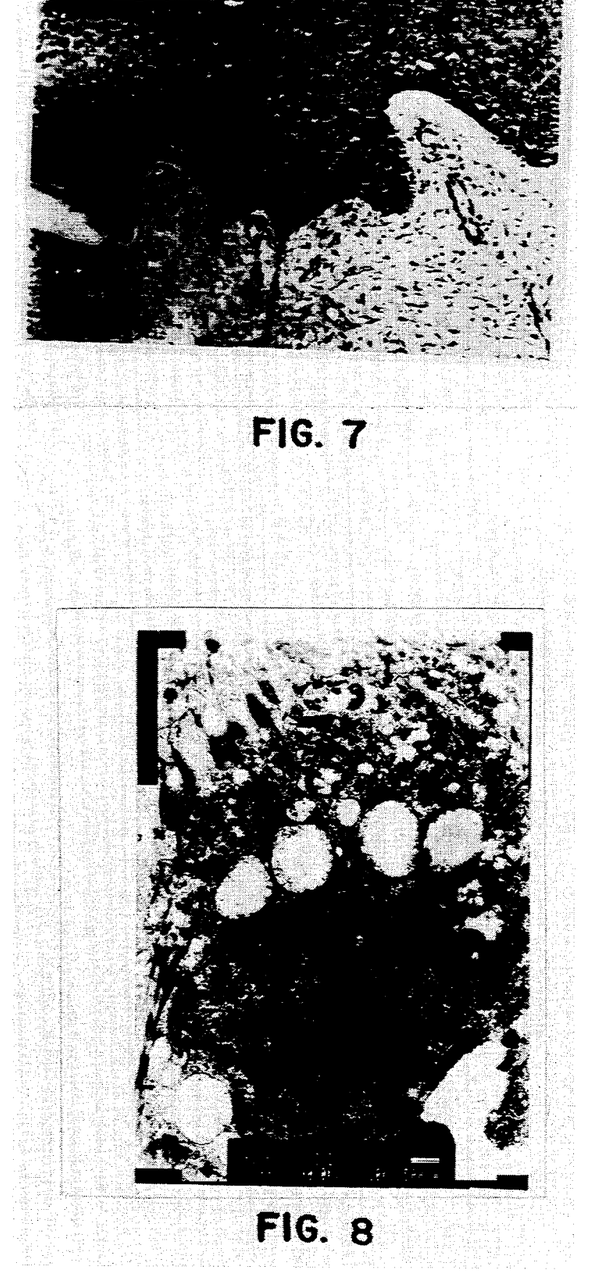
FIG. 7: Human skin with third degree burn treated with the pharmaceutical composition of the invention. Burn skin tissue after treatment, seen under optical microscope.
FIGS. 8, 9 and 10: Human skin with third degree burn, seen before treatment, under electron microscope.
Figure 9:
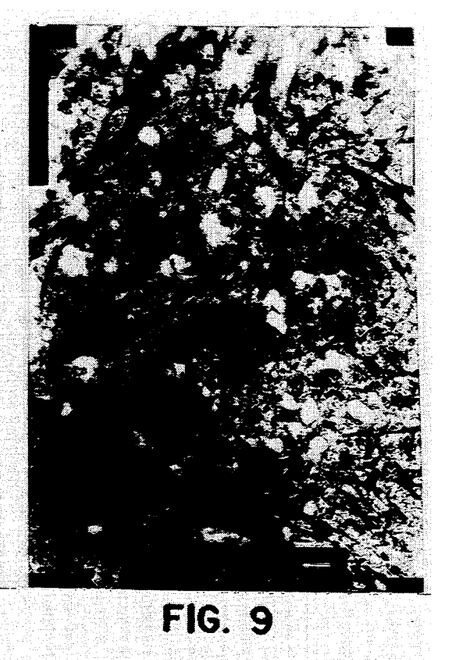

After treatment: (FIG. 7). The burned skin had recovered to normal. Newly grown capillaries and fibroblasts were seen in the dermis layer.
Electron Micrographs Before treatment: (FIG. 8, 10,000×; FIG. 9, 10,000× and FIG. 10, 8,000×).

Figure 10:
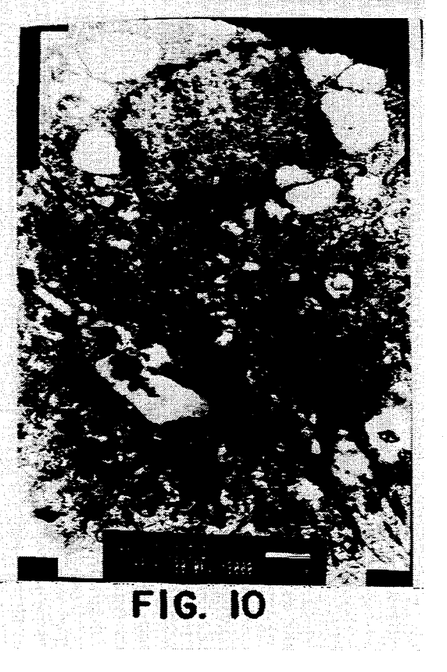

There were many spherical vacuoles around the cell nucleus. Nuclear surfaces were irregular. Entoblast had vanished. The thickness of elastic fibers in the dermis layer were not uniform and the arrangement of the fibers was not in order. There were deposits in the cell.

Figure 11:
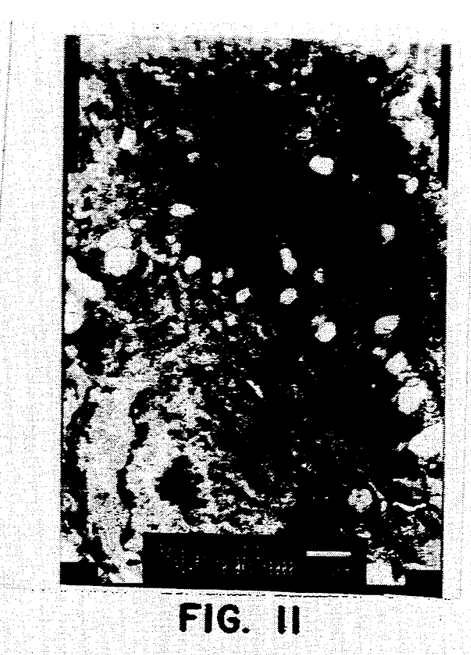
FIGS. 11, 12 and 13: Human skin with third degree burn treated with the pharmaceutical composition of the invention, seen under electron microscope.
Figure 12:
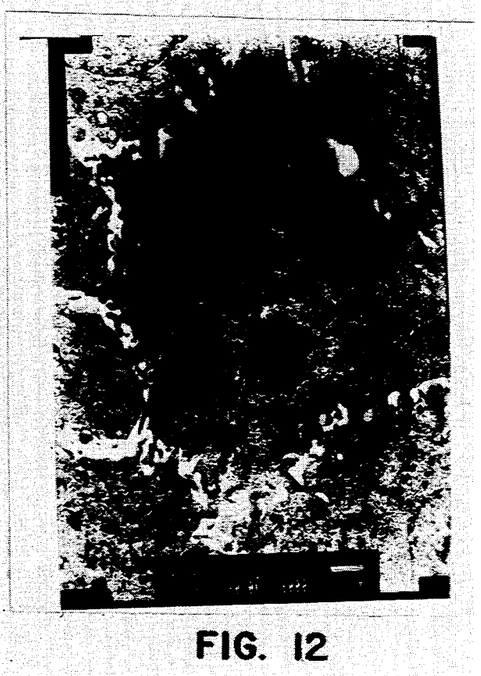
Figure 13:
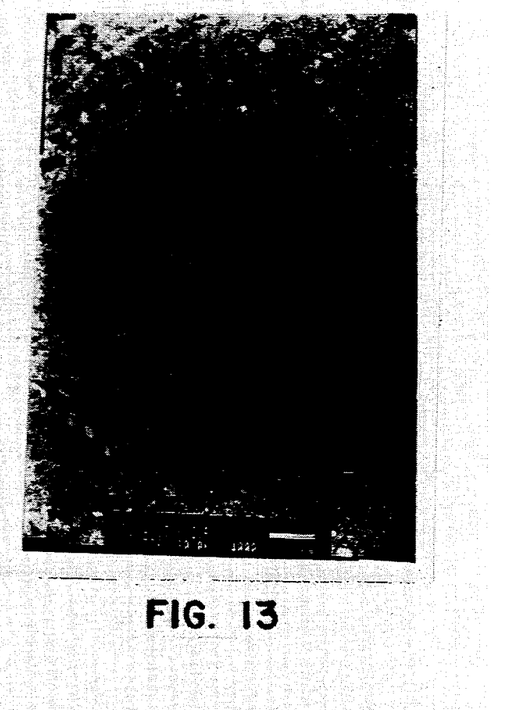

After treatment: (FIG. 11, 4,000×; FIG. 12, 6,000×; FIG. 13, 5,000×)

Cells arranged regularly and orderly in the prickle cell layer. Cell nuclei were clearly seen with entoblast. The distribution of nuclear chromatin was uniform. Bridge corpuscles were normally recovered.

EXPERIMENT 3

Pharmacodynamic Experiment

Antiinfective Effect

A. 7 guinea pigs were depilated on both sides of the back and scalded on the depilated areas. 2 days after scalded, the animals were inoculated with P. aeruginosa to both sides of the wounds (using the same method as for inoculation to culture medium). Wounds on one side were treated with the pharmaceutical composition of the invention described in example 3, 6 hours after inoculated. Wounds on the other side received no treatment. The results revealed that the untreated wounds had serious invasive infection of P. aeruginosa and wounds treated with the pharmaceutical composition of the invention had no infections. The experiment had been repeated for 4 times using 28 guinea pigs as a total. The results were the same.

B. 28 guinea pigs were randomly divided into 4 groups, 7 in each and were depilated and scalded as in A. Wounds on one side of the back were let to heal spontaneously (control group). Wounds on the other side were treated with the pharmaceutical composition of the invention (treating group). The animals were killed at different time intervals (3 days, 6 days, 10 days and 20 days after wounded) Bacteria counts on the living tissue underneath the wounds were as follows: (Table III)

TABLE III

|  | Treating | Control group | P |
|---|---|---|---|
| 3 days | 2.61 ± 1.14 × $10^3$ | 4.43 ± 2.09 × $10^3$ | <0.05 |
| 6 days | 3.81 ± 0.27 × $10^3$ | 3.24 ± 0.73 × $10^4$ | <0.001 |
| 10 days | 3.57 ± 0.64 × $10^3$ | 1.08 ± 0.10 × $10^5$ | <0.001 |
| 20 days | 2.82 ± 1.16 × $10^3$ | 7.02 ± 0.43 × $10^3$ | <0.05 |
| Normal tissue | 2.10 ± 0.52 × $10^3$ | 2.20 ± 0.63 × $10^3$ | >0.05 |

EXPERIMENT 4

Pharmacodynamic Experiment

Epithelialized Regeneration of Sweat Glands

Patients with superficial third degree burns of the same severity were treated. Half of the wounds were treated by covering with human anmiotic membrane and half of the wounds were treated with the pharmaceutical composition of the invention described in example 2. After treatment, skin pathological sections were examined under optical microscope.

Figure 14:
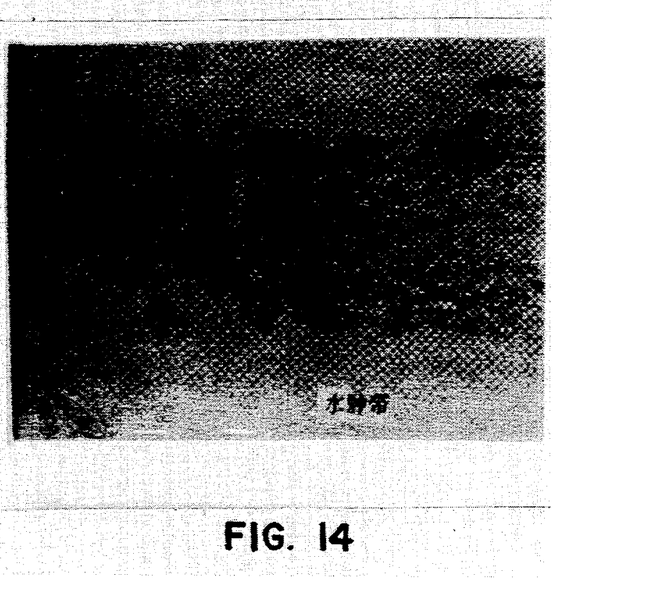
FIG. 14: Pathological section from patient with superficial third degree burn, covered with human amniotic membrane, seen under optical microscope.

Wounds healed by covering with human anmiotic membrane (FIG. 14) had 2 to 3 layers of epithelial cells covering the wounds. Underneath the wounds there were edema in the superficial layer of the dermis. Collagenous fibers were broken. No skin appendage was found.

Figure 15:
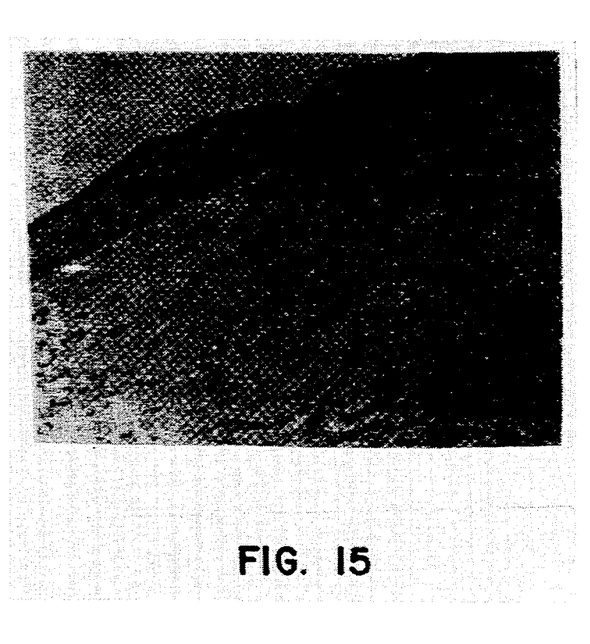
FIG. 15: Pathological section from patient in example 2, with superficial third degree burn treated with the pharmaceutical composition of the invention, seen under optical microscope.

Wounds healed by treating with the pharmaceutical composition of the invention (FIG. 15) had a complete whole layer of epithelium. The wound tissues were covered by squamous epithelium. Cells in the epithelial layer arranged orderly. New epithelium was formed. Residual sweat glands were seen in the dermal tissue.

EXPERIMENT 5

Pharmacodynamic Experiment

Wound Healing 21 guinea pigs were divided into 3 groups, 7 in each. Animals were depilated and scalded on both sides of the back to produce deep second degree wounds with a diameter of 2 cm. Wounds on one side were treated with the pharmaceutical composition of the invention described in example 2 and wounds on the other side were treated respectively with SD-Ag, badger fat, or sesame oil plus beeswax (97:3) as controls. Wound sizes were measured at different time intervals after treatment and healing times were recorded. Healing rates were calculated according to the equation:

$$\text{Healing rate (mm/day)} = \frac{\text{Healed wound area (mm}^2\text{)}}{\text{Healing time (day)}}$$

The results are summarized in Table IV

TABLE IV

| Controls | Healing rate of wounds treated with the pharmaceutical composition | Healing rate of wound treated with one of the control methods | P |
| --- | --- | --- | --- |
| SD—Ag | 1.1676 ± 0.0521 | 0.94441 ± 0.0592 | <0.001 |
| Badger fat | 1.0920 ± 0.0643 | 0.9295 ± 0.264 | <0.001 |
| Sesame oil plus beeswax | 1.0100 ± 0.0502 | 0.9154 ± 0.0480 | <0.05 |

The results revealed that wounds treated with the pharmaceutical composition of the invention healed more quickly than treated with other remedies.

50 patients burned or scalded, the largest lesion area was 20% BSA, were treated with the pharmaceutical composition of the invention. 20 patients burned or scalded, the largest lesion area was 10% BSA were treated with conventional exposed therapy. Comparison of the therapeutic effects including analgesic effect, healing time, infection rate, toxic reaction, mode of healing and self sensation of the wound, between the two groups were made. The results revealed that the pharmaceutical composition of the invention had good analgesic and antiinfective effects. It promoted healing of the wounds and had no toxic reaction.

200 patients with cervical erosion were treated with the pharmaceutical composition of the invention to give marked therapeutic results.

26 cases of wound ulcers due to different causes, among which the largest lesion area was 6% with a depth reaching periosteum. The longest time of the ulcers was 6 months and the shortest 4 months. The pharmaceutical composition of the invention was administered locally four times a day. The wounds heal in 15 to 20 days.

What we claim is:

1. A pharmaceutical composition for topically treating thermal injuries of warm blooded mammals including humans, said composition consisting of:
   beeswax in the amount of 3 to 15 weight percent, said beeswax containing less than 20 weight percent paraffin; and
   a sesame oil extract of ingredients in the dry state consisting of Huangqin, Huanglian, Huangbai, earthworm and poppy capsule, in which each of the ingredients is in an amount of 2 to 10 weight percent based upon the total weight of sesame oil, which extract is in an amount of 85–97 weight percent based upon the total weight of the composition, wherein said sesame oil contains water within the range of 1/1,000 to 1/10,000; and
   said pharmaceutical composition containing $\beta$-sitosterol extracted from said ingredients consisting of Huangqin, Huanglian, Huangbai, earthworm and poppy capsule.

2. A pharmaceutical composition according to claim 1 wherein said pharmaceutical composition contains $\beta$-sitosterol in the range of 0.20 to 1 weight percent of the total weight of pharmaceutical composition.

3. A pharmaceutical composition according to claim 1, wherein said earthworm is the whole worm dried or fresh.

4. A process for preparing the pharmaceutical composition described in claim 1, said process comprising the steps of:
   (1) cutting Huangqin, Huanglian and Huangbai into pieces and then mixed with earthworm and poppy capsule;
   (2) preheating sesame oil which contains water in the range of 1/1,000 to 1/10,000 to 120° C. to 180° C.;
   (3) adding the mixture of Huangqin, Huanglian and Huangbai, earthworm and poppy capsule into the preheated sesame oil to form a mixture having a proportion by weight of the said Huangqin, Huanglian, Huangbai, earthworm and poppy capsule to sesame oil in the range of 2–10 to 100, and boiling the mixture for 30 to 45 minutes;
   (4) cooling the heated mixture, separating the sesame oil from the mixture at ambient temperature, and discarding the residue to obtain a sesame oil extract containing active constituents of Huangqin, Huanglian, Huangbai, earthworm and poppy capsule; and
   (5) thoroughly mixing the sesame oil extract of step (4) with sufficient beeswax to obtain an 85–97 weight percent of the sesame oil extract containing 3–15 weight percent of beeswax, said beeswax containing less than 20 weight percent paraffin, to obtain the pharmaceutical composition, said pharmaceutical composition containing $\beta$-sitosterol extracted from said Huangqin, Huanglian, Huangbai, Earthworm and poppy capsule.

5. A process according to claim 4, wherein said earthworm is the whole worm dried or fresh.

6. A process according to claim 4 wherein pharmaceutical composition contains $\beta$-sitosterol extracted from said dry ingredients in an amount in the range of 0.20 to 1 weight percent based upon the total weight of the pharmaceutical composition.

7. A method for topically treating superficial ulcers of warm blooded mammals including humans comprising topically administering a sufficient amount of the pharmaceutical composition according to claim 1 to the ulcer area of mammals including humans to repair said ulcer.

8. A method for topically treating thermal injuries of warm blooded mammals including humans comprising topically administering a sufficient amount of the pharmaceutical composition according to claim 1 to the thermally injured area of mammals including humans to repair said injury.

9. A pharmaceutical composition for topically treating thermal injuries to mammals, including humans, said composition comprising:
   (a) beeswax in the amount of 3 to 15 weight percent, said beeswax containing less than 20 weight percent paraffin; and
   (b) a sesame oil extract of dry ingredients consisting of Huangqin, Hunaglian, Huangbai, earthworm and poppy capsule in which each of the ingredients is in an amount in the range of 2 to 10 weight percent based upon the total weight of sesame oil, which oil is in an amount in the range of 85–97 percent based on the total weight of the composition, wherein said sesame oil contains water in the range of 1/1,000 to 1/10,000;
   where said pharmaceutical composition contains $\beta$-sitosterol extracted from said Huangqin, Huanglian, Huangbai, earthworm and poppy capsule.

10. The composition according to claim 9 wherein said composition contains $\beta$-sitosterol derived from said dry ingredients in the amount in the range of 0.20 to 1 weight percent of the total weight of said pharmaceutical composition.

11. The pharmaceutical composition of claim 9 wherein said earthworm is fresh or dried whole earthworm.

12. A process for preparing the pharmaceutical composition described in claim 9, said process comprising the steps of:
   (1) cutting Huangqin, Huanglian and Huangbai into pieces and then mixing said pieces with earthworm and poppy capsule;
   (2) preheating sesame oil which contains water in the range of 1/1,000 to 1/10,000 to 120° C. to 180° C.;
   (3) adding the mixture of Huangqin, Huandlian, Huangbai, earthworm and poppy capsule to the preheated sesame oil to form a mixture having a proportion of said Huangqin, Huanglian, Huangbai, earthworm and poppy capsule to sesame oil in the range of 2–10 to 100, and boiling the mixture for 30 to 45 minutes;
   (4) cooling the heated mixture, separating the sesame oil from the mixture at ambient temperature, and discarding the residue to obtain a sesame oil extract containing active ingredients from Huangqin, Huanglian, Huangbai, earthworm and poppy capsule; and
   (5) thoroughly mixing 85–97 weight percent of the sesame oil extract obtained in step (4) with 3–15 weight percent of beeswax to obtain the pharmaceutical composition, said beeswax containing less than 20 weight percent paraffin
   wherein said pharmaceutical composition contains $\beta$-sitosterol extracted from said Huangqin, Huanglian, Huangbai, earthworm and poppy capsule.

* * * * *